United States Patent
Wang et al.

(10) Patent No.: US 9,630,925 B2
(45) Date of Patent: Apr. 25, 2017

(54) HSP90 INHIBITOR AND PREPARATION METHOD AND USE THEREOF

(75) Inventors: Yifei Wang, Guangzhou (CN); Guowen Xing, Guangzhou (CN); Huaiqiang Ju, Guangzhou (CN); Wenhui Lin, Guangzhou (CN); Chuiwen Qian, Guangzhou (CN); Min Xia, Guangzhou (CN); Xiaoping Zhou, Guangzhou (CN); Meiying Zhang, Guangzhou (CN)

(73) Assignee: Jinan University, Guangzhou, Guangdon (CN)

( * ) Notice: Subject to any disclaimer, the term of this patent is extended or adjusted under 35 U.S.C. 154(b) by 574 days.

(21) Appl. No.: 13/878,223

(22) PCT Filed: Feb. 16, 2011

(86) PCT No.: PCT/CN2011/071022
§ 371 (c)(1),
(2), (4) Date: Apr. 7, 2013

(87) PCT Pub. No.: WO2012/045237
PCT Pub. Date: Apr. 12, 2012

(65) Prior Publication Data
US 2013/0190509 A1     Jul. 25, 2013

(30) Foreign Application Priority Data
Oct. 8, 2010  (CN) .......................... 2010 1 0299615

(51) Int. Cl.
C07D 231/56     (2006.01)
A61K 31/416    (2006.01)
(52) U.S. Cl.
CPC .......... *C07D 231/56* (2013.01); *A61K 31/416* (2013.01)

(58) Field of Classification Search
None
See application file for complete search history.

(56) References Cited

U.S. PATENT DOCUMENTS 7,358,370 B2     4/2008   Huang
2007/0207984 A1  9/2007   Huang

OTHER PUBLICATIONS

International Search Report issued Jul. 8, 2011 by the State Intellectual Property Office, the P.R. China acting as the International Searching Authority for PCT/CN2011/071022. (Chinese).
Written Opinion issued Jul. 8, 2011 by the State Intellectual Property Office, the P.R. China acting as the International Searching Authority for PCT/CN2011/071022. (Chinese).
English translation of Written Opinion issued Jul. 8, 2011 by the State Intellectual Property Office, the P.R. China acting as the International Searching Authority for PCT/CN2011/071022. (Chinese).
English translation of the abstract of "The effects of a novel Hsp90 inhibitor—SNX-2112 on hepatis metablic enzymes in rats," May 2010, 26:5, pp. 585-588.
English translation of the abstract of CN101967125A, Feb. 9, 2011.
English translation of the abstract of CN101219963A, Jul. 16, 2008.
English translation of the abstract of CN1896060A, Jan. 17, 2007.

Primary Examiner — Kamal Saeed
(74) Attorney, Agent, or Firm — Latimer IP Law, LLC

(57) ABSTRACT

Disclosed are an Hsp90 inhibitor and a preparation method and use thereof. The Hsp90 inhibitor is 2-(4-(3-acetylcarnitineacyloxy)cyclohexylamino)-4-(1-(3,6,6-trimethyl-4-oxy-4,5,6,7-tetrahydroindazole))benzamide. The Hsp90 inhibitor has good water solubility and high bioavailability, and can effectively inhibit the proliferation of cancer cells, such as leukemia, cervical cancer, breast cancer, human laryngeal epithelial carcinoma, or malignant melanoma cells. It can also effectively inhibit the activity of herpes simplex virus. The maximal non-toxic concentration of the Hsp90 inhibitor on normal cells is a high, and the Hsp90 inhibitor only has specific inhibition effect on cancer cells.

4 Claims, 1 Drawing Sheet

HSP90 INHIBITOR AND PREPARATION METHOD AND USE THEREOF

BACKGROUND OF THE INVENTION

Field of the Invention

The present invention relates to the biomedical field, and particularly relates to a novel Hsp90 inhibitor and a preparation method and use thereof.

Description of Related Art

Heat shock proteins (Hsps) are a class of proteins produced by cells under some stress conditions, such as heat shock, glucose starvation, or pathogenic microorganism infection. They are also widely distributed in normal state cells. Hsps are a family of highly conserved proteins expressed in organisms during evolution, which, as molecular chaperones, are involved in the protection of cells against various stimuli (including cold, hot, anoxia, heavy metal ion, virus infection, etc.). Hsps mainly are involved in folding and transporting nascent peptide chains in cells, and identifying denatured proteins, thus playing a role in regulating cell growth, differentiation, and survival. Hsps are not only involved in the critical physiology processes, such as stress protection, signal transduction, immune response, development, and differentiation, etc., but also relate to the formation of various diseases, such as infection, autoimmune disease, atherosclerosis, tumor, etc.

Based on their molecular weight, Hsps can be divided into 5 large families, i.e., Hsp100s, Hsp90s, Hsp70s, Hsp60s, and small Hsps. Hsp90s are one of the most active molecular chaperones in cells, and are widely involved in signal transduction, hormone response, and transcription regulation processes in cells. The main functions of Hsp90s are maintaining protein stability in cells, improving the resistance of cells against stresses, enhancing antioxidation reactions, and maintaining the normal physiologic function of cells. Hsp90s, themselves, do not involve in the constitution of the target protein. Hsp90s are cytoplasmic proteins, and in mammalian cells, the Hsp90 family consists of 3 members: cytoplasmic chaperone Hsp90-a (inducible type/major type) and Hsp90-b (constitutive type/minor type), analogue endoplasmic reticulum chaperon GRP94 (glucose-related protein 94), and mitochondrial homolog Hsp75/TRAP1 (tumor necrosis factor receptor-associated protein 1). When a stress occurs, Hsp90s can interact with those proteins whose conformations are changed due to the environment stimuli, so as to ensure the proper folding of the proteins and prevent them from the nonspecific aggregation, thus maintaining the normal activity of the cell. Before transmembrane transporting, the proteins must be unfolded, and after transmembrane transporting, they will be refolded to form mature types. Hsp90s, as molecular chaperones, have the unfoldase function, which can identify and bind hydrophobic surfaces that are partially exposed after a proteins unfolds, so as to prevent the interaction from agglomeration, until the transmembrane delivery is finished.

Abnormal activation and mutation proliferation signal molecules that exist in tumor cells have to combine with Hsp90s to stabilize their structure, thus maintaining the growth advantageous properties of tumor cells. In tumor cells, Hsp90s are mainly in the activated state, and in normal cells, they are mainly in the latent state. When in the activated state, Hsp90s can form complexes with the receptor proteins and auxiliary molecular chaperones, Hsp70, Hsp40, Hop (Hsp70 organizing protein), p23, CDC37, etc., thus maintaining the receptor proteins in the mature functional conformations, and protecting the receptor proteins from degradation by proteasomes.

In the normal state, Hsp90s are expressed at low levels, are regulated by the cell cycle, and mainly exist in the cytoplasm. When a stress occurs, Hsp90s rapidly enter the cell nucleus, and induced synthesis of Hsp90s is up-regulated at both the transcription and translation levels, which can increase the anti-stress ability of the cell. However, in tumor cells, Hsp90s show a sustaining high induced expression. Such high expression does not require thermal stimulus, mutation, or abnormal protein, which are known to stimulate the synthesis of Hsp90s. The high levels of Hsp90s is one of the reasons for tumor cells to be hypersensitive to Hsp90 inhibitors.

In 1999, Klein first proposed a tumor multi-point-attack (Multi-enzyme-targeted) theory. The core of such a theory was to use a target site to achieve a multiple point block on the tumor signal pathway network, thus completely destroying the whole signal pathway network on which the tumor depended for survival. Therefore, finding the effective target was a key for applying the tumor therapy. The inhibitor based on molecular chaperones did not directly act on the kinase itself, but inhibited the associated molecular chaperone which maintained the active conformation of the kinase, through the ubiquitin-proteasome pathway, a large amount of kinases were degraded by proteasomes, thus deactivating the signal transduction pathway mediated by the kinases and failing to receive the signal from upstream. As compared with the direct inhibitor of conventional kinases, the inhibition of a single target of Hsp90s can simultaneously produce the feature of multipath antitumor effects, which not only can use a single medicament but also can reduce the drug resistance occurrence, thus making Hsp90s the exciting molecular targets for tumor therapy.

In addition, Hsps also have an intimate relationship with virus infections. At present, it is proved that Hsps induced by a virus after infecting the host, can combine with the virus protein so as to form complexes. Such a process can be associated with virus replication. The Hsps produced by the host cell which are induced by various types of virus infection can combine with the virus protein in a plurality of links during virus replication, forming HSP-virus peptide complexes, facilitating correct folding of the virus protein, facilitating transmembrane transport and virus assembly, maturing of the virus, etc. Thus, it is advantageous for virus replication.

It was reported that herpes simplex virus can induce an Hsp70 of 70 Kda, which required the synthesis of early virus protein, but did not require the replication of the virus DNAs. Hsp70 was expressed at a low level in non-stress rodent cells, but HSV infection can induce its expression. Within 4 hours after the HSV-1 and HSV-2 infections, the levels were increased. The Hsp70 synthesis and accumulation were increased in the infected cells, the UV irradiated HSV-1 lost the activity for inducing Hsp70, and the inhibition on virus DNAs did not affect the induction to Hsp70, but the protein synthesis within 2 hours after infection was necessary for inducing Hsp70.

Herpes simplex virus, which belongs to herpes virus family, and a herpes virus subfamily, was the first discovered human herpes virus, and was divided into two serotypes, i.e., type I (HSV-1) and type II (HSV-2). The herpes simplex virus infection is quite widespread, which mainly infringes skin, mucous membranes, and nervous tissue, thus causing the infection in human and many animals. HSV-1 generally infects the skin and the mucous membrane of the mouth, lips, eyes, and the central nervous system, occasionally the genital organ; HSV-2 generally relates to the genital organ infection and the neonatal infection.

At present, due to the lack of an efficient virus vaccine, drug therapy has become a main approach for treating HSV infection. In the clinic, the common therapeutic drugs are mainly nucleosides such as acycloguanosine, etc., whose target is the viral DNA polymerase, which in turn effects the replication of the virus. At present, the widely used ones are acycloguanosine analogues, with Acyclovir (ACV) as a representative, comprising Acyclovir, Valaciclovir, Penciclovir, Famciclovir and Ganciclovir. In addition, there are also nonnucleoside analogues, with sodium pyrophosphate as a representative. But part of the nucleoside analogues, such as Iododeoxyuridine, trifluorothymidine, arabinosyladenosine, and Ganciclovir, and the like, has mutagenicity, and low safety. And in the 1980s, an ACV resistant strain was discovered, and it was determined that in bone marrow transplantation patients and HIV patients, drug resistant strains were more likely to occur. Therefore, there is a need to find an antivirus drug with a new mechanism of action, and due to the critical role of Hsp90 in virus infection, it also becomes a potential antivirus target.

The first Hsp90 inhibitor drug, geldanamycin (GA), is a benzoquinone drug which was originally screened as an anti-fungal agent. GA is a specific Hsp90 inhibitor. Its structure is mainly formed by connecting a benzoquinone part and a planar macrocyclic Ansa bridge. One study revealed that its antitumor ability depended on the degradation of the tumorigenic protein kinase in the proteasome, but GA has high toxicity to kidney and liver, which may be attributed to its off-target effect. During screening low toxic derivatives at the National Cancer Institute (NCI), and it was found that 17-allylaminogeldanamycin (17-AAG) wherein one side chain of GA was replaced, had all of the characteristics of GA, including the inhibition effect and the antitumor activity of Hsp90, but had lower toxicity. However, 17-AAG had poor water solubility, and cannot be applied orally. Subsequently, a novel derivative of GA (17-dimethylaminoethylamino-17-demethoxygeldanamycin, 17-DMAG) was developed. This compound presented good water solubility and oral bioavailability, and has entered Phase II/III clinic trials for solid tumor and hematologic malignancy.

Radicicol, a macrocyclic antibiotic separated from Monosporium Bonorde, has the potential to reverse malignant phenotypes, which is similar to GA, and plays a role in the Hsp90 receptor protein degradation. Radicicol can reverse the deterioration degree of fibrous cells transfected with v-src and v-Ha-Ras. Radicicol binds to the N-terminal area of Hsp90, and has good antitumor activity in vitro, but has no antitumor ability in vivo, which is mainly attributed to its chemical structure being unstable, and prone to degradation after entering the body. Recently, studies have shown that Novobiocin can significantly decrease the levels of p185erb2, p60v-src, Raf-1, and mutant p53 in cells. It has also been demonstrated in a point mutation experiment that Novobiocin is a C-terminal inhibitor of Hsp90. The studies of Neckers et al., showed that 3 Coumermycins compounds (Novobiocin, Chlorobiocin, Coumermycin A1) all significantly decreased the levels of P185erb2, p60v-src, hypoxia inducible factor 1, and mutant P53 in cells. Novobiocin is a Coumermycin antibiotic which has been used in the clinic and has little toxicity and has good pharmacokinetic characteristics. Novobiocin is a C-terminal inhibitor of Hsp90, and has an inhibitory effect on various of cancer cells. It can be applied in combination with an anticancer drug to reverse the drug resistance to the anticancer drug, but the concentration of Novobiocin used as an inhibitor of Hsp90 is up to 700 μM, which also limits its further development as an antitumor drug in vivo.

In addition to the several Hsp90 inhibitors described above, recently some Hsp90 inhibitors have been synthesized and screened successively. PU3, a purine-scaffold Hsp90 inhibitor, is a micromolecular compound designed based on the result from X-ray crystal diffraction. The action site of PU3 is consistent with that of GA, which acts on the ATP/ADP binding site at the N-terminal of Hsp90, and PU3 is also similar to GA in terms of the inhibition of Hsp90 receptor protein degradation and antitumor ability. PU3 is modified and improved so as to form a derivative thereof, which binds the N-terminal of Hsp90, with an affinity of 30 times higher than that of PU3, but its activity is less than that of 17-AAG. However, the derivative does not present a specific accumulation between cells, but such a characteristic is typical for the more hydrophobic GA derivative. IPI-504 (17-AAG hydroquinone), is mainly aimed at the multiple myeloma treatment, which currently has entered Phase I clinic trials. The compound has high water solubility and can be converted into the active form of 17-AAG in the body. However, the anticancer mechanism thereof is still under research now. NVP-AUY922 is an isoxazole derivative, which also belongs to a micromolecular Hsp90 inhibitor, and has a potential therapeutic effect on the ER- and ERBB2-positive breast cancer patients.

SUMMARY OF THE INVENTION

In order to overcome the disadvantages and deficiencies in the prior art, the primary object of the present invention is to provide a novel Hsp90 inhibitor.

Another object of the present invention is to provide a method for preparing the above-mentioned Hsp90 inhibitor.

Yet another object of the present invention is to provide use of the above-mentioned Hsp90 inhibitor.

The objects of the present invention can be achieved by the following technical solution:

An Hsp90 inhibitor, is 2-(4-(3-acetylcarnitineacyloxy) cyclohexylamino)-4-(1-(3,6,6-trimethyl-4-oxy-4,5,6,7-terahydroindazole))benzamide (2-acetoxy-4-(4-(2-carbamoyl-5-(3,6,6-trimethyl-4-oxo-4,5,6,7-tetrahydro-1H-indazol-1-yl)phenylamino)cyclohexyloxy)-N,N,N-trimethyl-4-oxobutan-1-aminium chloride), with a code of Xbj-B16-1, and the structural formula thereof is shown in Formula I.

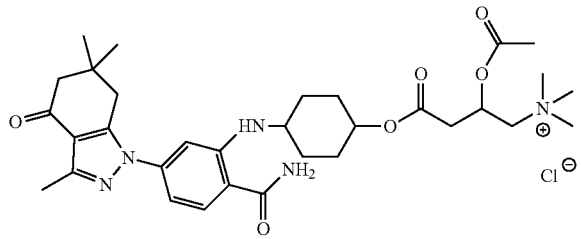

(Formula I)

The method for preparing the above-mentioned Hsp90 inhibitor, comprises the steps of:

The compound of Formula III (labelled in the reaction scheme below as "3") is mixed with the compound of Formula II (labelled in the reaction scheme below as "2") in a molar ratio of 2:1, and reacted for 3-5 hours under stirring at 20-30° C.; then the reaction is quenched, the product is extracted, the extracted organic layer is dried, and the solvent is removed under reduced pressure, so as to obtain the Hsp90 inhibitor of Formula I.

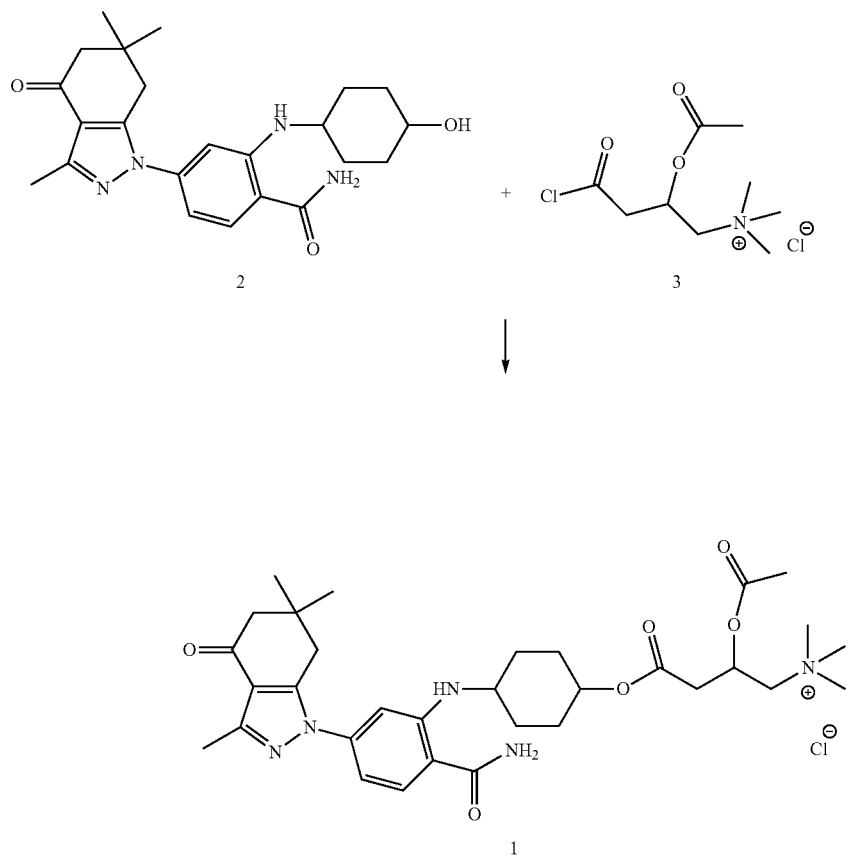

The above-mentioned Hsp90 inhibitor can be used for preparing an antitumor or antivirus drug.

Said tumor is leukemia, cervical cancer, breast cancer, human laryngeal epithelial carcinoma, or malignant melanoma.

Said virus is herpes simplex virus.

Xbj-B16-1 uses benzamide as a basic backbone, and the side chain is provided with various of substituent groups. Such a novel structure is different from any Hsp90 inhibitor disclosed before. It is demonstrated through X-ray diffraction that such a novel structure can competitively bind to the ATP site on Hsp90, and can effectively inhibit the binding between the protein and the purine. It is demonstrated through experiments that Xbj-B16-1 can inhibit the proliferation of various solid tumors and leukemia cells in vitro, and induce the apoptosis thereof.

The present invention has the following advantages and beneficial effects as compared with the prior art:

(1) Xbj-B16-1 can effectively inhibit the proliferation of cancer cells, such as leukemia, cervical cancer, breast cancer, human laryngeal epithelial carcinoma, and malignant melanoma, etc., and can effectively inhibit the activity of herpes simplex virus.

(2) The maximum non-toxic concentration of Xbj-B16-1 on normal cells is high, and Xbj-B16-1 only has specific inhibition effect on cancer cells.

(3) Xbj-B16-1 has good water solubility, and high bioavailability.

DETAILED DESCRIPTION OF VARIOUS EMBODIMENTS OF THE INVENTION

Figure 1:
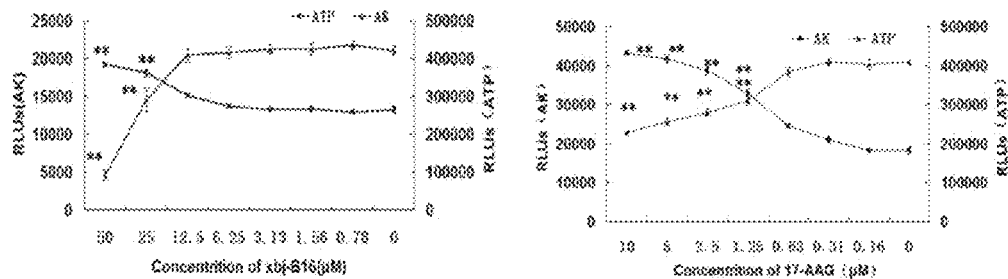
FIG. 1 presents graphs showing the toxicity determination results of the drugs on a normal cell (Vero), wherein the left shows results for Xbj-B16-1, and the right shows results for the antitumor positive drug 17-AAG.

The present invention is further described in detail below in combination with the examples and drawings, but the embodiments of the present invention are not limited thereto.

Example 1

Preparation of the Hsp90 Inhibitor, Xbj-B16-1

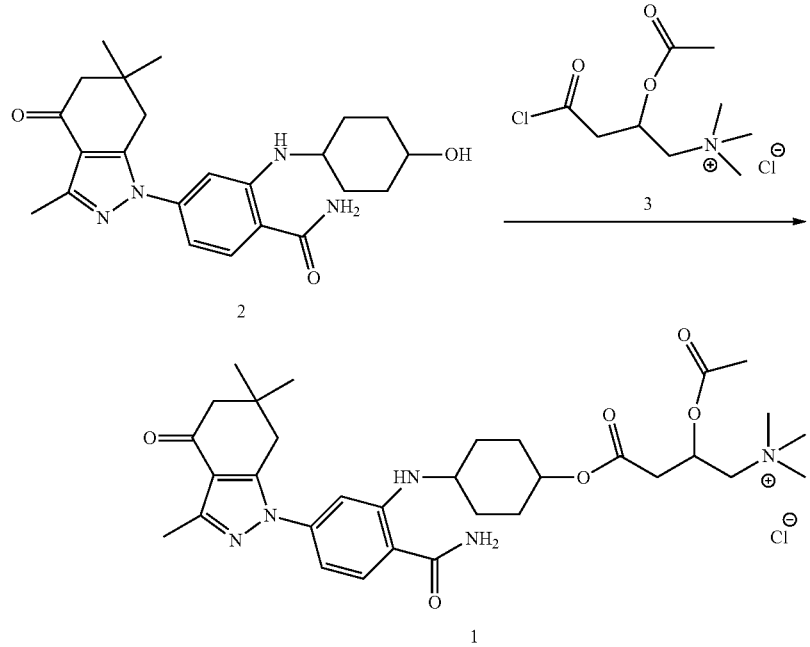

(1) The process for the synthesis of the compound of Formula II (i.e., compound "2") can be found in Chinese Patent ZL 200610087495.1;

(2) The process for the synthesis of the compound of Formula III (i.e., compound "3") can be found in "Organic Chemistry", 2006, vol. 26, pp. 946-949, and Chinese Patent Application CN 200810014212.X;

(3) The process for the synthesis of the Hsp90 inhibitor (i.e., compound "1") is as follows. The compound of Formula III (0.13 g, 0.5 mmol) was placed into a 25 mL eggplant shaped flask, then the compound of Formula II (0.01 g, 0.25 mmol) and 5 mL dichloromethane were added therein, and they were reacted under stirring at 25° C. for 4 hours. 10 mL of a mixture solution of saturated sodium bicarbonate and saline were added to quench the reaction, the product was extracted with 200 mL dichloromethane, and the organic layer was dried with anhydrous $MgSO_4$. The solvent was removed under reduced pressure, thus obtaining a solid product (50 mg, 25%).

The structural characteristic data of the product was as follows:

1H NMR ($CDCl_3$, 400 MHz) δ: 1.11 (s, 6H), 1.32 (m, 2H), 1.46 (m, 2H), 2.09 (m, 4H), 2.41 (s, 2H), 2.55 (s, 3H), 2.82 (s, 2H), 3.48 (s, 9H), 4.07 (m, 1H), 4.39 (m, 1H), 4.79 (m, 1H), 5.67 (m, 1H), 6.63 (d, J=8.3 Hz, 1H), 6.80 (s, 1H), 7.55 (d, J=8.5 Hz, 1H). MS (ESI) m/z: 596.2 (M)+. It is demonstrated that the structure of the obtained product was as shown in Formula I.

Example 2

Half Lethal Dose of Xbj-B16-1 on 5 Types of Tumor Cell Strains

In this example, the positive control was 17-AAG (purchased from Alexis Biochemicals Company, US); and the applied cell lines of K562, Hela, A375, Mcf-7, etc., were all purchased from ATCC, Manassas, Va., USA.

(1) Xbj-B16-1 was dissolved with $H_2O$, and formulated into a 2 mM stock solution, and stored at 4° C.

(2) Human cervical carcinoma cells (Hela), human malignant melanoma cells (A375), human laryngeal epithelial cancer cells (Hep-2), and human breast cancer cells (MCF-7) in logarithmic growth phase were taken, and regulated into single cell suspensions having a cell concentration of $2\times10^5$/mL with a DMEM culture medium containing 10% fetal bovine serum (purchased from GIBCO BRL, US). Then the single cell suspensions were seeded into 96 well plates, 100 μL/well. The cells were cultured overnight, making them attach to the wall. The culture solutions were discarded, and 100 μL of the culture medium containing various Xbj-B16-1 sample concentrations (20 μM, 10 μM, 5 μM, 1 μM, 0.1 μM, and 0.05 μM, respectively) were added into each of the wells. Quadruplicate wells were set for each of the concentrations, and the experimental groups, the solvent control groups, and the blank groups were set for the experiments. The 96 well plates were placed in an incubator at 37° C., 5% $CO_2$, and incubated for 48 hours.

Human chronic myeloid leukemia cells (K562) in logarithmic growth phase were taken, and regulated into a single cell suspension having a cell concentration of $4\times10^5$/mL with a RPMI1640 culture medium containing 10% fetal bovine serum (purchased from GIBCO/BRL, US), 50 μL of the single cell suspension and 50 μL of the culture medium containing various Xbj-B16-1 sample concentrations (40 μM, 20 μM, 10 μM, 2 μM, 0.2 μM, and 0.1 μM, respectively) were added to each of the wells. Quadruplicate wells were set for each of the concentrations, and the experimental groups, the solvent control groups, and the blank groups were set for the experiments. The 96 well plates were placed in an incubator at 37° C., 5% $CO_2$, and incubated for 48 hours.

(3) With reference to the MTT method established by Mosmann, 20 μL, MTT solution was added to each of the wells and incubation continued for 4 hours. The solution in each well was sucked out and discarded carefully. Then 100 mL DMSO was added to each of the wells, and the mixture shaken for 15 minutes on a shaker in the dark. The colorimetric measurements were carried out on a microplate reader (with a wavelength of 570 nm, and a reference wavelength of 630 nm), and the absorbances (A value) were determined. The half toxic concentration (IC50) of the drug was calculated. The growth inhibition rate was calculated according to the following equation: growth inhibition rate (%)=(1−A570/630 in experimental group/A570/630 in solvent control group)×100. The half inhibition concentration (IC50) value of the drug on the cell was calculated by the Modified Karber method, and the calculation equation for the Modified Karber method was: 1 g IC50=Xm−I[P−(3−Pm−Pn)/4].

[Xm: 1 g maximum dose; I: 1 g (maximum dose/adjacent dose); P: the sum of the positive reaction rates; Pm: the maximum positive reaction rate; Pn: the minimum positive reaction rate.]

The result of the half inhibition concentration (IC50) of the drug on the cell strain is shown in Table 1.

TABLE 1

IC50 Values of Xbj-B16-1 On Various Tumor Cell Strains

| | IC50 (μM) | |
|---|---|---|
| Cell strain | Compound Xbj-B16-1 | Positive drug 17-AAG |
| human chronic myeloid leukemia cell (K562) | 8.31 ± 1.78 | 2.43 ± 0.68 |
| Human breast cancer cells (MCF-7) | 9.53 ± 2.03 | 3.24 ± 0.15 |
| Human cervical carcinoma cell (Hela) | 10.35 ± 2.48 | 5.42 ± 0.18 |
| Human malignant melanoma cell (A375) | 7.23 ± 1.31 | 3.13 ± 0.15 |
| Human laryngeal epithelial cancer cell (Hep-2) | 6.37 ± 2.13 | 2.33 ± 0.30 |

From the results shown in Table 1, it can be seen that Xbj-B16-1 has significant inhibitory effects on the proliferation of human cervical carcinoma cells (Hela), human malignant melanoma cells (A375), human breast cancer cells (MCF-7), human laryngeal epithelial cancer cells (Hep-2), and human chronic myeloid leukemia cells (K562), but the inhibitory effects on the proliferation were lower than that of the positive drug 17-AAG.

Example 3

In Vitro Toxicity Test of Xbj-B16-1 on Normal Cells (African Green Monkey Kidney Cells, Vero)

Vero cells in logarithmic growth phase were taken and regulated into a single cell suspension having a cell concentration of $2×10^5$/mL with a DMEM culture medium containing 10% fetal bovine serum (purchased from GIBCO/BRL, US), and seeded into 96 wells plates, 100 μL/well. The cells were cultured overnight, and the culture solutions were discarded. 100 μL of the culture medium containing 50 μM, 25 μM, 12.5 μM, 6.25 μM, 3.13 μM, 1.57 μM, and 0.63 μM of Xbj-B16-1 respectively were added into each of the wells. Then the Vero cells were incubated for an additional 48 hours. The ATP levels in the Vero cells and the AK release quantity in the supernatant of the culture solutions were determined using kits from Lonza, US (Vialight HS kit and Toxilight bioassay kit). The maximum non-toxic concentration of the drug on the Vero cells within 48 hours were then assayed. The positive drug 17-AAG was used as control in the experiment (starting from 10 μM, double dilution of 6 concentrations). The results of the experiment are shown in FIG. 1.

The results of FIG. 1 show that the maximum non-toxic concentration of Xbj-B16-1 on normal cells (African green monkey kidney cell, Vero) was 12.5 μM, which was much less sensitive than that on cancer cells. The toxicity of Xbj-B16-1 was lower than that of the positive drug, 17-AAG (the non-toxic concentration of 17-AAG is 0.63 μM), which illustrated that the in vitro toxicity of the drug was low. Thereby it can be seen that Xbj-B16-1 had specific inhibitory effect on cancer cells.

Example 4

Activity of Xbj-B16-1 Against Herpes Simplex Virus Observed Using CPE Method

In this example, the Vero cell line (ATCC CCL81, purchased from ATCC, US) was used as the normal cell. The herpes simplex virus comprised Herpes Simplex Virus Type 1 Strain F (HSV-1 F, ATCC VR-733), and Herpes Simplex Virus Type II Strain 333 (HSV-2 333). Various concentrations of Xbj-B16-1 (starting from 25 μM, double dilution of 6 concentrations) and the positive drug ACV (starting from 10 μM, double dilution of 6 concentrations) were mixed with each 50 μL of HSV-1 or HSV-2 virus dilute solution (100TCID50) respectively, then directly added to a single layer of Vero cells, and incubated in an incubator at 37° C., 5% $CO_2$ for 48 hours. The cytopathic effect (CPE) was then observed under an optical microscope.

Figure 2:
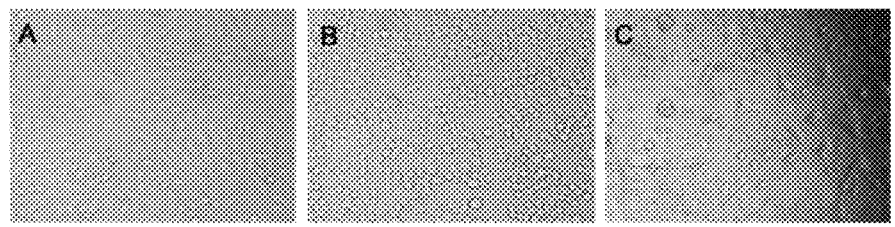
FIG. 2 presents graphs showing the cytopathic effects caused by HSV-1 and HSV-2 (100×), wherein Panel A shows effects on a normal cell, Panel B shows the cytopathic effect caused by HSV-1, and Panel C shows the cytopathic effect caused by HSV-2.
Figure 3:
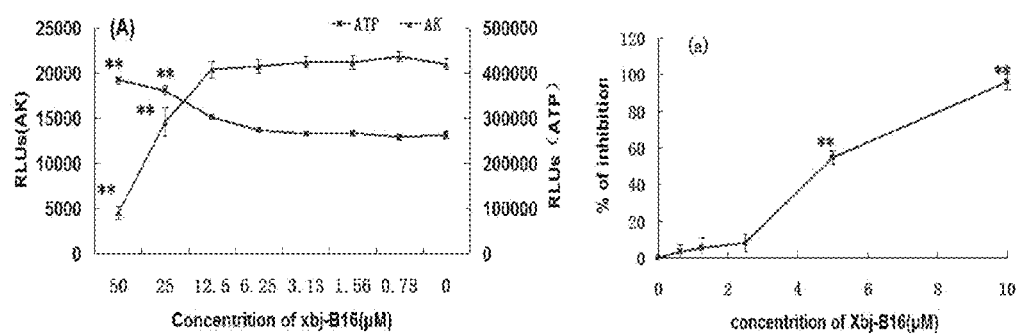
FIG. 3 presents graphs showing the toxicity and anti-HSV activity determination results of the drug of the present invention on Vero cells, wherein Panel (A) shows toxicity determination result of the drug on the cells, and Panel (a) shows plaque statistical results of the drug against HSV.

Under the microscopic observation, the normal cells showed a spindle shape, a clear cell membrane boundary, a good cytoplasmic transparency, and a complete cell morphology (as seen in FIG. 2, Panel A). The CPE characteristics caused by HSV-1 were cell swelling, rounded and shriveled, fusion, fallout, and disruption (as seen in FIG. 2, Panel B), and the multinucleated giant cell or the cell fusion formed by HSV-2 were more significant (as seen in FIG. 2, Panel C).

The statistical results of the CPE are shown in Tables 2 and 3. The compound Xbj-B16-1 had some effects against Herpes Simplex Virus Type I and against Herpes Simplex Virus Type II, at 12.5 μM. It can not only inhibit the cytopathic effect caused by HSV-1, but also have some inhibition on the cytopathic effect caused HSV-2, but the inhibitory effect was lower than that of the positive drug ACV.

TABLE 2

The inhibition effect of Xbj-B16-1 on HSV-1

| Xbj-B16-1 | Concentration (μM) | 12.5 | 6.25 | 3.13 | 1.56 | 0.78 | 0.39 | Virus control |
|---|---|---|---|---|---|---|---|---|
| | CPE | − | ++ | +++ | ++++ | ++++ | ++++ | ++++ |
| ACV | Concentration (μM) | 5.00 | 2.50 | 1.25 | 0.63 | 0.31 | 0.16 | ++++ |
| | CPE | − | − | − | − | ++ | ++ | ++++ |

Note:
CPE degree: 0-25% +, 26%-50% ++, 51%-75% +++, 76%-100% ++++.

TABLE 3

| | | The inhibition effect of Xbj-B16-1 on HSV-2 | | | | | | |
|---|---|---|---|---|---|---|---|---|
| Xbj-B16-1 | Concentration (μM) | 12.5 | 6.25 | 3.13 | 1.56 | 0.78 | 0.39 | Virus control |
| | CPE | + | +++ | +++ | ++++ | ++++ | ++++ | ++++ |
| ACV | Concentration (μM) | 5.00 | 2.50 | 1.25 | 0.63 | 0.31 | 0.16 | ++++ |
| | CPE | − | − | − | − | ++ | ++ | ++++ |

Note:
CPE degree: 0-25% +, 26%-50% ++, 51%-75% +++, 76%-100% ++++.

Example 5

The Combined Effects of Xbj-B16-1 Against Herpes Simplex Virus Determined Using Plaque Reduction Assay (PRA)

In this example, the Vero cell line (ATCC CCL81, purchased from ATCC, US) was used as the normal cell. The herpes simplex virus comprised Herpes Simplex Virus Type I Strain F (HSV-1 F, ATCC VR-733), Herpes Simplex Virus Type II Strain 333 (HSV-2 333).

The Vero cells were cultured to a monolayer on 24 well plates. The culture solutions were discarded, then each 100 μL of the virus dilute solutions (HSV-1 and HSV-2) (50 PFU/well) and 10 μM, 5 μM, 2.5 μM, 1.25 μM, 0.63 μM of Xbj-B16-1 were added, and incubated in an incubator at 37° C., 5% $CO_2$ for 2 hours. The virus solutions were suck out and discarded. Then 1 mL of a cell maintenance medium (covering solution) containing 0.5% carboxymethyl cellulose was added, triplicate wells were set for each of the concentrations, and the virus control groups and the normal cell control groups were set. After observing for 72 hours, they were fixed for 30 minutes with 10% formaldehyde, stained for 30 minutes with 1% crystal violet, rinsed with water, and dried. The plaques were counted with reference to Nitta's method, and the plaque inhibition rate was calculated.

A curve graph was plotted with the logarithmic value of the drug concentration as the horizontal coordinate, and the plaque inhibition rate as the vertical coordinate. Further, a sensitivity curve of the virus on the drug was plotted according to the results of the plaque inhibition rate, and a half inhibition concentration (IC50) of the drug was calculated. The plaque inhibition rate=(the plaque number in the virus control group−the plaque number in the drug treated group)/(the plaque number in the virus control group)× 100%.

The determination results of the toxicity and the anti-HSV activity of the drug are shown in Table 3 (above). The experimental result statistics of the drug against herpes simplex virus are shown in Table 4. From these results, it can be seen that the drug Xbj-B16-1 had some anti-HSV effect, but such effect was less than that of the positive drug ACV.

TABLE 4

The anti-HSV activity and the therapeutic index of Xbj-B16-1 (, n = 3)

| | Toxicity[a] | | Antiviral activity[b] (μM) | | |
|---|---|---|---|---|---|
| Com- | | (μM) | HSV-1 | | HSV-2 | |
| pound | $TC_0$ | $TC_{50}$ | $IC_{50}$ | $TI^c$ | $IC_{50}$ | $TI^c$ |
| Xbj-B16-1 | 12.5 | 47.79 ± 3.53 | 2.96 ± 0.56 | 16.14 | 3.2 ± 0.33 | 14.93 |
| ACV | — | >100 | 4.16 ± 1.02 | >240.38 | 3.32 ± 0.44 | >301.20 |

$TC_{50}$: half lethal concentration £» $TC_0$: the maximum non-toxic concentration; $IC_{50}$: 50% pathologic inhibition concentration; TI: therapeutic index ($TC_{50}/IC_{50}$)

The above-mentioned examples are the preferred embodiments of the present invention, but the embodiments of the present invention should not be limited thereto. Any other changes, modifications, substitutions, combination, and simplification are all the equivalent replacements, and should be encompassed in the protection scope of the present invention, without departing from the spirit and principle of the present invention.

The invention claimed is:

1. An Hsp90 inhibitor, characterized in that said Hsp90 inhibitor is 2-(4-(3-acetylcarnitineacyloxy)cyclohexylamino)-4-(1-(3,6,6-trimethyl-4-oxy-4,5,6,7-tetrahydroindazole)) benzamide, with a structural formula of Formula I:

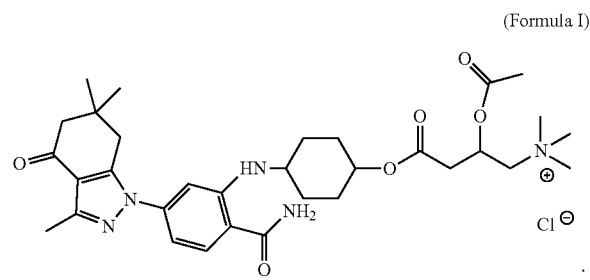 [SMILES: CC(=O)OC(CC(=O)OC1CCC(Nc2cc(-n3nc(C)c4c3CC(C)(C)CC4=O)ccc2C(N)=O)CC1)C[N+](C)(C)C ; [Cl-]]

(Formula I)

2. A method for preparing an Hsp90 inhibitor of claim 1, said method comprising the steps of:

mixing the compound of Formula III with the compound of Formula II in a molar ratio of 2:1;

reacting the mixture for 3-5 hours with stirring at 20-30° C.;

quenching the reaction;

extracting the product as an organic layer;

drying the extracted organic layer; and removing solvent under reduced pressure so as to obtain the Hsp90 inhibitor of Formula I;

wherein the reaction participants and the product have the following structures in which labels 1, 2, and 3 correspond respectively to Formulas I, II, and III:

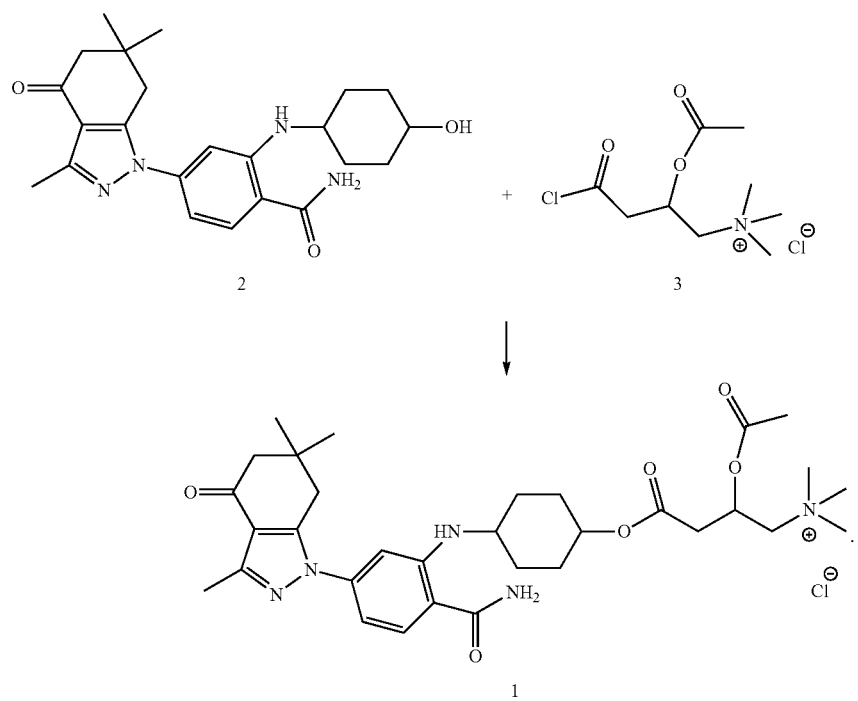
3. The Hsp90 inhibitor of claim 1, which is an antitumor drug, wherein a tumor targeted by the antitumor drug is leukemia, cervical cancer, breast cancer, human laryngeal epithelial carcinoma, or malignant melanoma.
4. The Hsp90 inhibitor of claim 1, which is an antivirus drug, wherein a virus targeted by the antivirus drug is herpes simplex virus.
* * * * *